(12) United States Patent
Gruber

(10) Patent No.: US 6,918,153 B2
(45) Date of Patent: Jul. 19, 2005

(54) SONIC POWER TOOTHBRUSH WITH MULTIPLE CONTAINERS

(75) Inventor: Paul Gruber, Bodensdorf (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 284 days.

(21) Appl. No.: 10/071,384

(22) Filed: Feb. 8, 2002

(65) Prior Publication Data

US 2002/0108193 A1 Aug. 15, 2002

(30) Foreign Application Priority Data

Feb. 12, 2001 (EP) .............................................. 01200508

(51) Int. Cl.[7] .............................................. A61C 17/22
(52) U.S. Cl. ............................. 15/22.1; 15/24; 401/46; 601/162; 433/89
(58) Field of Search ................. 15/221, 24, 29; 401/44, 45, 46, 47; 601/161, 162, 163, 164, 165, 166, 47, 46, 70, 72, 73, 75; 141/2, 18, 104, 98, 114; 320/114, 115; 433/80, 89, 216

(56) References Cited

U.S. PATENT DOCUMENTS 4,060,870 A    12/1977  Cannarella ..................... 15/24
5,286,192 A  *  2/1994  Dixon .......................... 433/80
5,321,866 A  *  6/1994  Klupt .......................... 15/22.1
5,474,451 A    12/1995  Dalrymple et al. ............ 433/80
6,648,641 B1 * 11/2003  Viltro et al. .................. 433/80

FOREIGN PATENT DOCUMENTS

EP         0565598 B1   10/1993   ........... A61C/15/00
WO         WO0041645     1/2000   ........... A61C/17/36

* cited by examiner

Primary Examiner—Robert J. Warden, Sr.
Assistant Examiner—Shay L Balsis

(57) ABSTRACT

An oral care system (1) comprising a sonic power toothbrush (2) which comprises a body (3), a brush member (4) mounted on the body (3), a brush head (5) which is supported by the brush member (4) at its end remote from the body (3) so as to be able to vibrate relative to the body (3) and which is provided with bristles (6) and an additive outlet (7), an additive container (8) connected to said additive outlet (7), driving means (9) for generating sonic frequency vibrations, and transmission means (29) for transmitting said sonic frequency vibrations to the brush head (5), wherein the toothbrush (2) comprises at least one further additive container (18). Instead of the user having to apply a first and a second additive manually to the brush head (5), these additives are already incorporated into the sonic-power toothbrush (2), which benefits the user-friendliness of the device. The application of the additives to the teeth is realized in an effective manner, while the sonic frequency vibrations enhance the effect of the additives.

10 Claims, 3 Drawing Sheets

SONIC POWER TOOTHBRUSH WITH MULTIPLE CONTAINERS

Figure 1:
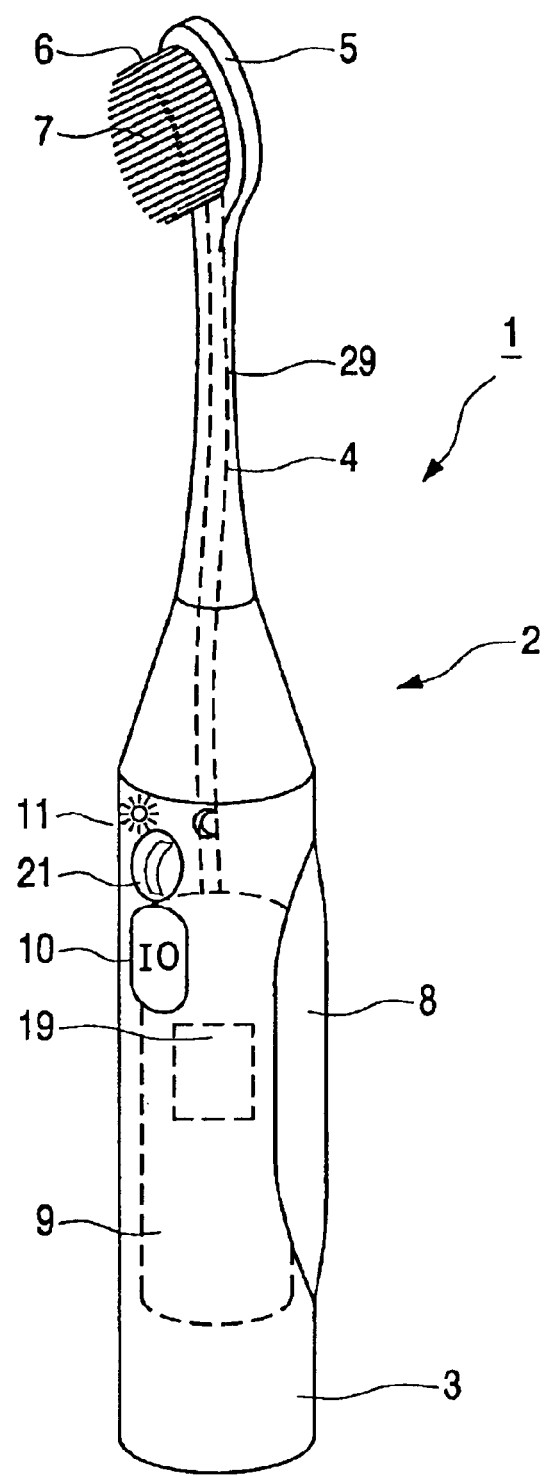

The invention relates to an oral care system comprising a sonic power toothbrush which comprises a body, a brush member mounted on the body, a brush head which is supported by the brush member at its end remote from the body so as to be able to vibrate relative to the body and which is provided with bristles and an additive outlet, an additive container connected to said additive outlet, driving means for generating sonic frequency vibrations, and transmission means for transmitting said sonic frequency vibrations to the brush head.

An oral care system comprising a sonic power toothbrush of the type defined in the opening paragraph is known from EP 0565598 B1.

In the known oral care system, the sonic power toothbrush comprises a brush head which is supported by the brush member at its end remote from the body so as to be able to vibrate relative to the body. The toothbrush further comprises an additive container from which during operation an additive is transported to the additive outlet, here formed by a number of hollow bristles on the brush head. When the toothbrush is activated, the brush head and the bristles provided thereon are set into vibration by the driving means. The vibration of the brush head and the bristles is used to scrub the teeth mechanically. At the same time the vibration of the brush head provides sonic-frequency vibrations which are sufficient to support cavitation and streaming throughout the oral cavity, including areas beyond the reach of the bristle contact area. The sonic frequency vibrations delivered by the toothbrush enhance the effect of an additive on the teeth and oral cavity, especially if this additive is a medicinal agent.

It is an object of the invention to provide an improved oral care system comprising a sonic power toothbrush.

To achieve this object, an oral care system comprising a sonic power toothbrush according to the invention is characterized in that the system comprises at least one further additive container. At least two different types of additives can thus be stored in the toothbrush. The user does not have to apply a first and a second additive manually to the brush head, since these additives are already incorporated into the toothbrush. This benefits the user-friendliness of the device. The application of at least two additives to the teeth is realized in an effective manner by means of only one device, while the sonic frequency vibrations enhance the effect of the additives. This offers a large number of possibilities of use. During operation, for example, subsequent first and second additive flows from the first and the second container, respectively, to the additive outlet can take place. During the first additive flow, for example, a cleaning additive may be transported to the additive outlet in the brush head and may then be applied to the teeth via this brush head. The cleaning additive adds to the cleaning effect of the scrubbing movement of the bristles, while the sonic frequency vibrations enhance the penetration of the cleaning additive into areas between the teeth. The second additive flow may, for example, comprise transport of an additive chosen from a group of additives for treatment and protection of the oral cavity and teeth from the second container to the additive outlet. The first and the second additive flow may, for example, also take place simultaneously during operation. This is advantageous in cases where certain additives have a beneficial effect on teeth when applied in combination with each other, but cannot be stored together owing to, for example, unwanted chemical reactions. The combined application of the additives to the teeth takes place in an effective manner because the mixing of the additives during application to the teeth is enhanced by the sonic frequency vibrations.

An embodiment of an oral care system comprising a sonic power toothbrush according to the invention is characterized in that the toothbrush is provided with means for selection of a first and a second additive flow. The user of the system can thus make a selection as to which additive flow is to be started up. This offers a freedom of use because the user can determine, for example, whether all additive flows should take place and can choose the order in which the flows take place.

It is advantageous when said means comprise a switch which is movable into a first and a second position corresponding to the first and the second additive flow, respectively.

It is furthermore advantageous when an oral care system comprising a sonic-power toothbrush according to the invention comprises a processor for selecting and activating additive flows in the toothbrush. Depending on the type of additives being supplied by the toothbrush, it may be advantageous that the additive flows are selected automatically without user influence. The user then only starts up the brushing action of the toothbrush, while the processor further controls the additive transport. This is advantageous, for example, if the additives are medicinal agents that are to be applied in a certain quantity and order to have the correct effect on the teeth and oral cavity.

An embodiment of an oral care system comprising a sonic power toothbrush according to the invention is characterized in that the system comprises a charging holder in which the toothbrush can be placed for electrical charging, which holder is provided with a refill unit for refilling at least one of the containers when the toothbrush is placed in the holder. The toothbrush needs to be placed in the holder for electrical charging of its batteries after a certain period of use. If this holder is provided with a refill unit for refilling at least one of the containers, the period of inactivity of the toothbrush needed for recharging is further utilized for filling the container with a quantity of additive used up during the preceding period of use.

It is advantageous if the refill unit comprises at least one tank connected to a pump unit, which pump unit is connectable to at least one of the containers via a coupling when the toothbrush is placed in the holder.

Figure 2:
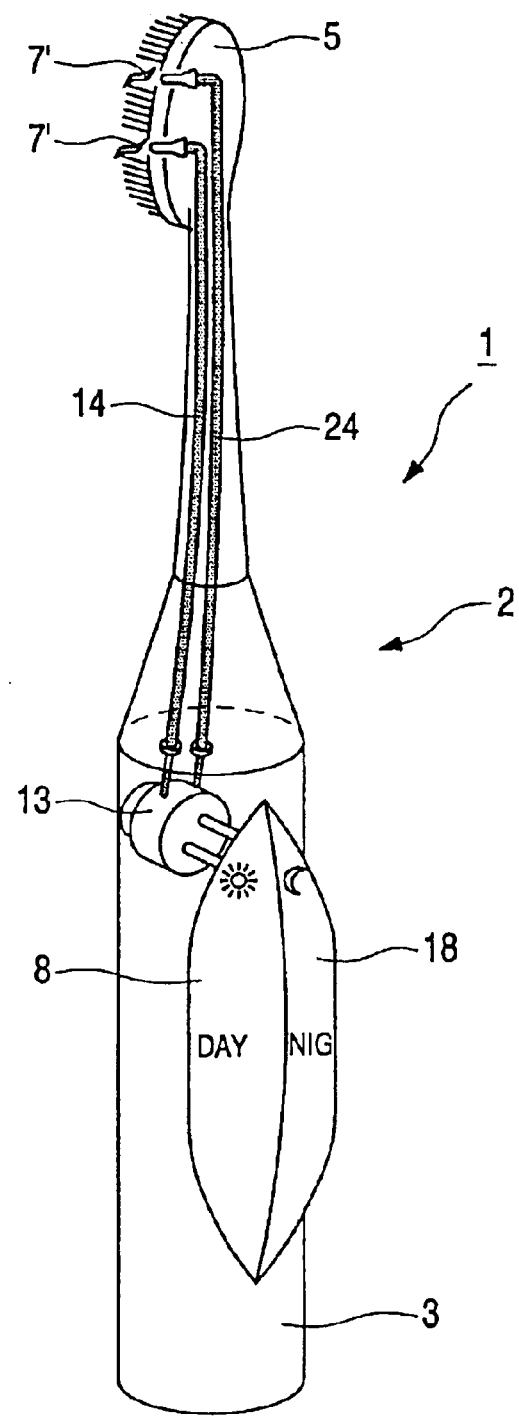
Figure 3:
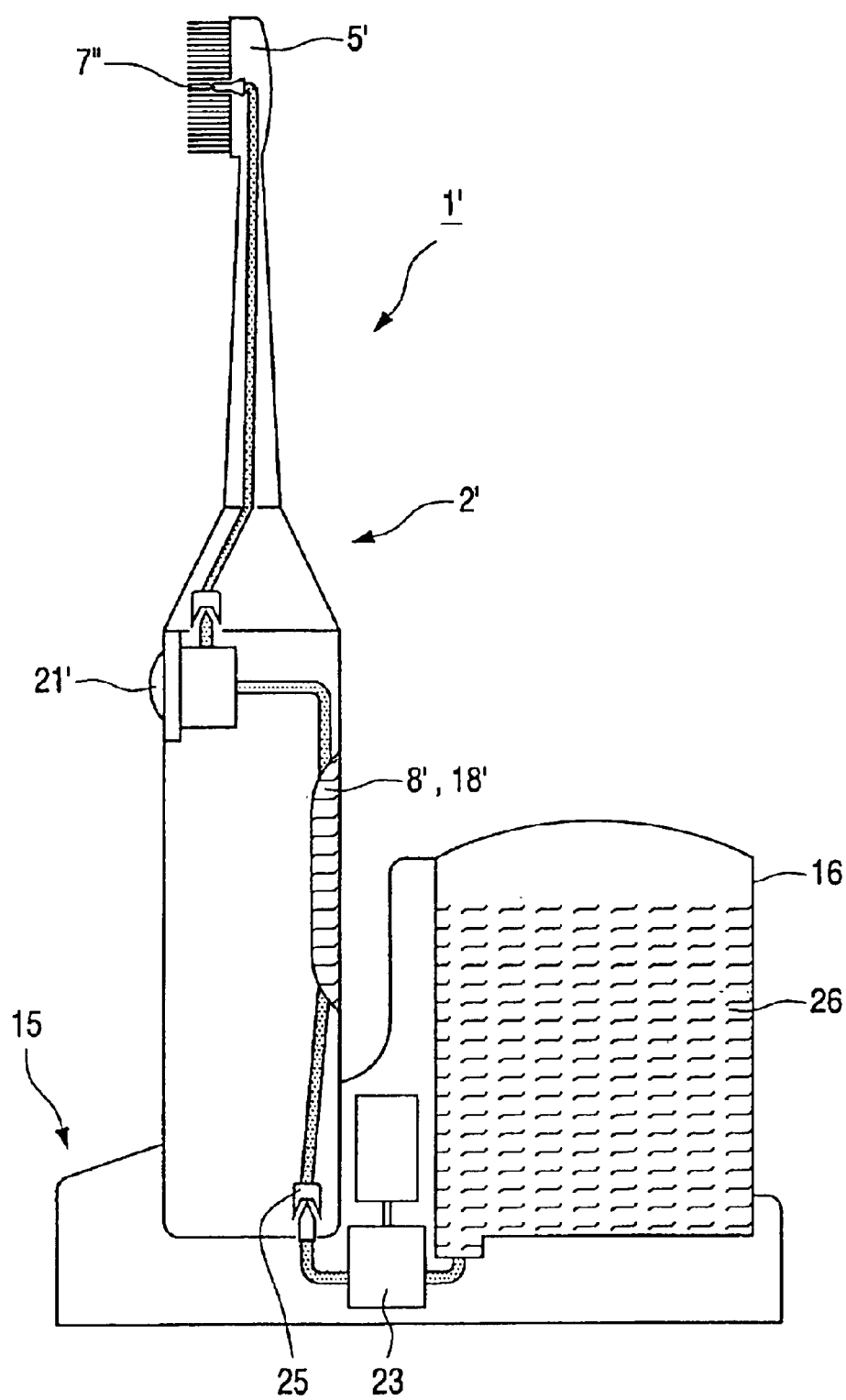

The invention will be described in more detail hereinafter with reference to the drawings, in which FIG. 1 is a perspective view of a first embodiment of an oral care system comprising a sonic power toothbrush according to the invention, FIG. 2 diagrammatically shows the toothbrush of FIG. 1, partly broken away, FIG. 3 diagrammatically shows a second embodiment of an oral care system comprising a sonic power toothbrush according to the invention.

FIG. 1 is a perspective view of a first embodiment of an oral care system 1 comprising a sonic power toothbrush 2 according to the invention. Said toothbrush 2 comprises a body 3 and a brush member 4 mounted on the body 3. Said brush member 4 carries at its end remote from the body 3 a brush head 5 mounted so as to be able to vibrate relative to the body 3, as described, for example, in EP 0565598 B1. Said brush head 5 is provided with bristles 6 and an additive outlet 7 which is shown in more detail in FIG. 2. The brush member 4 in this embodiment is mounted fixedly on the body 3, but it may alternatively detachably mounted so that the brush member 4 can be replaced with a new one when the bristles 6 are worn out. The toothbrush 2 furthermore comprises an additive container 8 connected to said additive outlet 7, which container in this embodiment is provided partly within the body 3 and partly protrudes from the circumferential surface of the body 3. The toothbrush 2 furthermore comprises driving means 9 for generating sonic frequency vibrations and transmission means 29 for transmitting said sonic frequency vibrations to the brush head 5. These driving and transmission means are shown diagrammatically in FIG. 1 and may comprise driving and transmission means as described, for example, in EP 0565598 B1. The driving means 9 may comprise drive electronics such as a power supply, an oscillator, an amplifier, and a transformer, but may alternatively comprise any other known type of driving means capable of generating sonic frequency vibrations. In this embodiment the power supply of the toothbrush 2 comprises rechargeable batteries, not shown in the figure, which can be electrically charged in a charging holder in which the toothbrush is placed after a certain period of use. In this embodiment, the body 3 is further provided with an on/off button 10 to activate and de-activate the driving means 9.

As can be seen in FIG. 2, the toothbrush 2 comprises a further additive container 18 next to the additive container 8, which containers are both in connection with the additive outlet 7 formed by openings 7' in the brush head 5. The containers are connected to these openings 7' via a pump unit 13 and respective transport channels 14 and 24. The first container 8 may contain a certain type of additive, and the further container 18 may contain different type of additive. During operation consecutive first and second additive flows take place from the first and the second container 8 and 18, respectively, via the pump unit 13 and the transport channels 14 and 24 to the additive outlet 7. Thus the toothbrush 2 applies two different additives to the teeth during operation, without the user having to apply these additives manually to the brush head 5 of the toothbrush first. As can be seen in FIG. 1, the toothbrush 2 is provided with means 11 for selection of the first and the second additive flow, in this embodiment a switch 21 movable from a neutral position into a first and a second position corresponding to the first and the second additive flow. The pump unit 13 in this embodiment comprises an electrically driven pump which is activated by a processor 19. The processor activates the pump unit 13 into pumping from one of the containers in dependence on the input from this switch 21 when the driving means 9 are activated by means of the on/off button 10. It is furthermore possible that the switch 21 is omitted and that, when the driving means 9 are activated by means of on/off button 10, the processor 19 starts to control the additive flow from the first and the second container in a certain order and with certain quantities. The user merely has to activate the toothbrush by pushing the on/off button 10, and the processor takes care of the additive supply. This adds to the user-friendliness of the toothbrush and makes it especially suitable for elderly people and children.

It is observed that the pump unit 13 in the toothbrush can also be manually driven by the user pushing a pump button which is provided on the body of the toothbrush next to the on/off button. It is also possible that, for example, a first additive is manually pumped to the brush head 5 by the user by means of the pump button, and the processor controls a further transport of a second additive to the brush head 5 after a certain period of time has passed. Furthermore, it is possible to apply sonic frequency vibrations during one of the additive flows only, while the other additive is applied without sonic frequency vibrations.

It is advantageous when the first additive flow comprises the transport of a cleaning additive from the first container 8 to the additive outlet 7, and the second additive flow comprises the transport of an additive chosen from a group of additives for treatment and protection of the oral cavity and teeth from the second container 18 to the additive outlet 7. In the embodiment of FIGS. 1 and 2, the first and the second additive flow comprise the transport of additives having a cleaning and a treating effect, respectively, on the teeth and the oral cavity, and are divided into a day and a night phase. In this embodiment, the body 3 of the toothbrush 2 is provided with symbols next to the switch 21 indicating the day and night phase. The day phase in this embodiment comprises the application of a cleaning additive, here formed by a gel, to the teeth during operation of the toothbrush. This phase is activated during the toothbrushing action of a user in the morning. The sonic frequency vibrations of the toothbrush enhance the cleaning effect of the cleaning gel. The night phase in this embodiment comprises the application of a revitalizing gel to the teeth during operation of the toothbrush. This phase is activated during the toothbrushing action of a user in the evening before going to sleep. The gel forms a coating on the teeth which treats the teeth during sleep of the user. The first and second additive flow may alternatively comprise, instead of a day phase and a night phase, a cleaning phase and a treating phase, which occur within one utilization of the toothbrush, in contrast to the embodiment with the day and night phases related to a user's morning and evening tooth-brushing sessions, respectively. The treating phase may comprise the application of the revitalizing gel as described above, or the application of, for example, a fluoride mineral for protection of the teeth.

The first and the second additive flow may furthermore take place simultaneously during operation. This is advantageous if certain additives cannot be stored within one container because of a chemical reaction between them, which reaction is unwanted during storage. In combination with each other, however, these additives have a beneficial effect on the teeth and oral cavity because of this very chemical reaction. The first and the second container 8, 18 may each contain one of these additives. The processor 19 is able to activate the pump unit 13 into pumping from both additive containers simultaneously, and the additives are then transported via respective transport channels 14 and 24 to the brush head 5 of the toothbrush 2. The additives come together during their application to the teeth after leaving their respective openings which form the additive outlet 7. Thus the chemical reaction between the additives can have its beneficial effect on the teeth and oral cavity, while the mixing and reach of the additives is enhanced by the sonic frequency vibrations. In the embodiment described here, the construction of the toothbrush makes possible both the sequential and the simultaneous application of different additives. A toothbrush only capable of simultaneous application is another possibility, which may be realized in that the transport channels 14 and 24 are combined into one transport channel.

The containers 8 and 18 in this embodiment are disposable containers removably mounted on the body of the toothbrush. The containers may alternatively comprise permanent containers which are to be removed for individual refilling. Furthermore, at least one of the containers may be fixedly mounted on or in the body 3 and may be refilled with additive. This will be further elucidated below.

FIG. 3 shows a second embodiment of an oral care system 1' comprising a sonic power toothbrush 2' according to the invention. The system 1' comprises a charging holder 15 in which the toothbrush 2' can be placed for electrical charging of its rechargeable batteries, which holder 15 is provided with a refill unit 16 for refilling at least one of the containers 8', 18' when the toothbrush 2' is placed in the holder. Said refill unit 16 comprises at least one tank 26 connected to a refill pump unit 23, which refill pump unit 23 is connectable to at least one of the containers 8', 18' via a coupling 25 in the toothbrush 2' when the toothbrush 2' is placed in the holder. The container can thus be refilled after a period of use while the toothbrush 2' is positioned in the holder 15 for recharging.

It is noted that the refill unit for refilling an additive container as described above may also be used to advantage in other types of toothbrushes. These toothbrushes may comprise, for example, different driving means, and may be power toothbrushes not using sonic frequency vibrations, or even non-electrically driven toothbrushes. With non-electrical toothbrushes, the holder would be a specific holder performing a storage and refill function instead of a charging holder, since there are no batteries to be charged. The refill unit is also advantageously usable with toothbrushes which comprise only one additive container. Refilling of the at least one container may be electrically driven or may be manually driven by a user performing a pumping action by means of, for example, a button.

It is observed that the toothbrush may also comprise more than two containers. In this manner the toothbrush is able to apply even more types of additives to the teeth and oral cavity during operation. Next to enhancing the brushing action of the toothbrush by means of different additives, it is also possible to add, for example, a spraying function to the toothbrush. The additive to be sprayed is then contained in a further container within the toothbrush. In addition, it is also possible that the refill unit 16 comprises two or more tanks and two or more couplings for refilling the containers.

It is furthermore observed that the oral care system may comprise, next to the sonic power toothbrush or instead of this toothbrush, other oral care devices such as a water syringe device which comprise at least two additive containers. Such a water syringe device comprising at least two additive containers offers the possibility of applying various additives to the oral cavity such as, for example, first a cleaning additive followed by a refreshing additive. The advantages of at least two additive containers in an oral care system as mentioned above also apply when these containers are provided in an oral care device such as a water syringe device.

What is claimed is:

1. An oral care system (1), comprising a sonic power toothbrush (2) which comprises:
   a toothbrush body (3);
   a brush member (4) mounted on the toothbrush body;
   a brush head (5) which is supported by the brush member at its end remote from the toothbrush body, so as to be able to vibrate relative to the body, and which includes bristles (6) and an additive outlet (7);
   a plurality of additive containers (8, 18) containing additives;
   driving means (9) for generating sonic frequency vibrations and a transmission means (29) for transmitting said sonic frequency vibrations to the brushhead;
   a manual selection means for selecting one additive container and means for moving the additive in said one container by manual action through the additive outlet; and
   an automatic selection means for automatically selecting at least one additional additive container that automatically follows selection of the one additive container by said manual selection means, and means for moving the additive in the additional additive container, through the additive outlet.

2. An oral care system of claim 1, wherein said manual selection means includes a switch which is movable into a position corresponding to selection of the one container.

3. An oral care system of claim 1, wherein the automatic selection means includes a processor (19) for selecting and activating additive flow from the additional additive container.

4. An oral care system of claim 3, wherein the processor controls the selection and activation of additive flow after a selected period of time has elapsed since manual selection of the one additive container.

5. An oral care system of claim 1, further including a charging holder (15) in which the toothbrush can be placed for electrical charging, wherein the holder is provided with a refill unit (16) for refilling at least one of the containers when the toothbrush is placed in the holder.

6. An oral care system (1) comprising a sonic power toothbrush (2) which comprises:
   a toothbrush body (3);
   a brush member (4) mounted on the toothbrush body;
   a brushhead (5) which is supported by the brush member at its end remote from the toothbrush body, so as to be able to vibrate relative to the body, and which includes bristles (6), an additive outlet (7);
   a plurality of additive containers (8, 18) containing additives;
   driving means for generating sonic frequency vibrations and a transmission means for transmitting said sonic frequency vibrations to the brushhead during use of one additive; and
   means for applying another additive with non-sonic frequency vibrations, wherein the additive containers are manually or automatically selected during use of the toothbrush.

7. An oral care system of claim 6, including switch means (21) which is movable into a position corresponding to selection of an additive when the additive is manually selected.

8. An oral care system of claim 6, including a processor (19) for automatically selecting an additive.

9. An oral care system of claim 6, including a charging holder (15) in which the toothbrush can be placed for electrical charging, wherein the holder is provided with a refill unit (16) for refilling at least one of the containers (8, 18) when the toothbrush is placed in the holder.

10. An oral care system, comprising:
    a sonic toothbrush (2), in turn comprising:
    a toothbrush body (3);
    a brush member (4) mounted on the toothbrush body;
    a brushhead (5) which is supported by the brush member at its end remote from the body, so as to be able to vibrate relative to the body, and which is provided with bristles (6) and an additive outlet (7);
    an additive container (8) connected to said additive outlet;
    driving means (9) for generating sonic frequency vibrations and transmission means (29) for transmitting said sonic frequency vibrations to the brushhead, wherein the toothbrush includes at least two additive containers; and an integrated container refill and battery charging base apparatus, including a refill pump unit, the base apparatus configured to both refill at least one of the containers and to charge at least one rechargeable battery of the toothbrush upon receiving the toothbrush within a holder portion thereof.

* * * * *